US00PP33051P2

(12) United States Plant Patent
van Langen

(10) Patent No.: US PP33,051 P2
(45) Date of Patent: May 11, 2021

(54) ***ECHEVERIA* PLANT NAMED 'AMIECH1913'**

(50) Latin Name: ***Echeveria* hybrid**
Varietal Denomination: AMIECH1913

(71) Applicant: NovoAmi B.V., Heerhugowaard (NL)

(72) Inventor: Gerard van Langen, Heerhugowaard (NL)

(73) Assignee: NovoAmi B.V., Heerhugowaard (NL)

( * ) Notice: Subject to any disclaimer, the term of this patent is extended or adjusted under 35 U.S.C. 154(b) by 0 days.

(21) Appl. No.: 16/895,319

(22) Filed: Jun. 8, 2020

(30) Foreign Application Priority Data

Dec. 17, 2019 (QZ) ..... PBR 2019/3422

(51) Int. Cl.
*A01H 5/12* (2018.01)
*A01H 6/32* (2018.01)

(52) U.S. Cl.
USPC ..... Plt./373
CPC ..... *A01H 6/32* (2018.05)

(58) Field of Classification Search
USPC ..... Plt./373
CPC ..... A01H 6/32
See application file for complete search history.

*Primary Examiner* — Anne Marie Grunberg
(74) *Attorney, Agent, or Firm* — Samuel R. McCoy, Jr.

(57) ABSTRACT

A new and distinct *Echeveria* hybrid plant named 'AMIECH1913' which is characterized by strongly concave obovate to short spatulate foliage in a basal rosette, green foliage that is lightly covered with light greyed-green epicuticular wax, and the stability of these characteristics from generation to generation.

4 Drawing Sheets

Latin name of the genus and species: The Latin name of the genus and species of the novel variety disclosed herein is *Echeveria* hybrid.

Variety denomination: The inventive variety of *Echeveria* hybrid disclosed herein has been given the variety denomination 'AMIECH1913'.

CROSS REFERENCE TO RELATED APPLICATIONS

This application claims priority to the Community Plant Variety Rights application number 2019/3422, filed Dec. 17, 2019, which is herein incorporated by reference.

BACKGROUND OF THE INVENTION

Parentage: 'AMIECH1913' is an interspecific hybrid seedling selection resulting from the controlled pollination of *Echeveria gilva* 'Green Gilva' (not patented), the seed parent, with an unnamed *Echeveria desmetiana* (not patented), the pollen parent. The crossing was made by the inventor in the spring of 2017 at a commercial greenhouse in Heerhugowaard, the Netherlands. In the winter of 2017, one seedling was observed which exhibited unique growth and foliage characteristics. The seedling was isolated for further evaluation in order to confirm the distinctness and stability of the characteristics first observed. Upon confirmation of distinctness and stability, 'AMIECH1913' was selected for commercialization.

Asexual Reproduction: Asexual reproduction of the new cultivar 'AMIECH1913', by way of rooting leaf cuttings, was first initiated in the summer of 2018 at the inventor's commercial greenhouse in Heerhugowaard, the Netherlands. Through three subsequent generations, the unique features of this cultivar have proven to be stable and true to type.

SUMMARY OF THE INVENTION

The cultivar 'AMIECH1913' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'AMIECH1913'. These characteristics in combination distinguish 'AMIECH1913' as a new and distinct *Echeveria* hybrid cultivar:

1. 'AMIECH1913' exhibits strongly concave obovate to short spatulate foliage in a basal rosette; and
2. 'AMIECH1913' exhibits green foliage that is lightly covered with light greyed-green epicuticular wax.
3. 'AMIECH1913' exhibits durable foliage.

BOTANICAL DESCRIPTION OF THE PLANT

Figure 1:
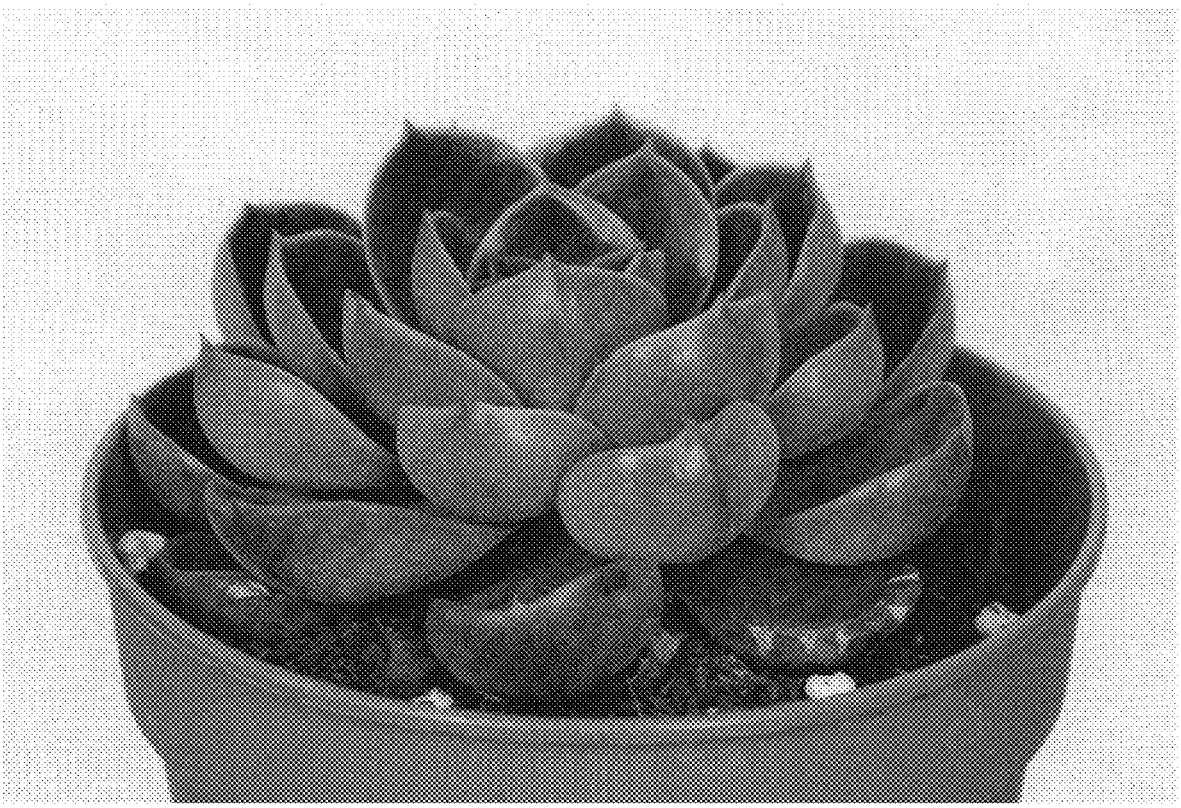
FIG. 1 illustrates, as nearly true as it is reasonably possible to make the same in color photographs of this type, an exemplary plant of 'AMIECH1913' grown in a commercial greenhouse in Heerhugowaard, the Netherlands. This plant is approximately 8 months old, shown planted in an 11 cm container.
Figure 2:
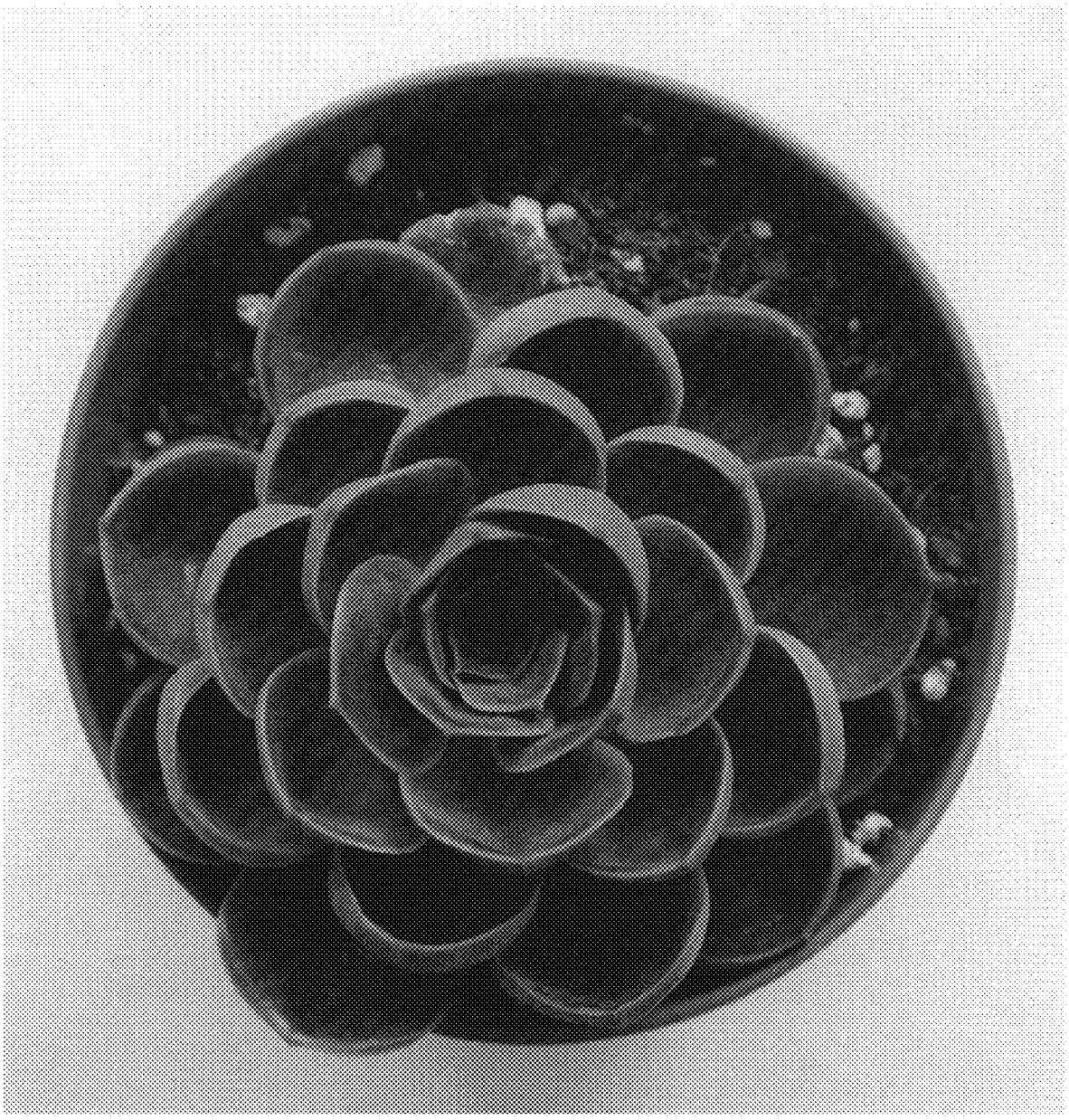
FIG. 2 illustrates, as nearly true as it is reasonably possible to make the same in color photographs of this type, the typical foliage arrangement of 'AMIECH1913.
Figure 3:
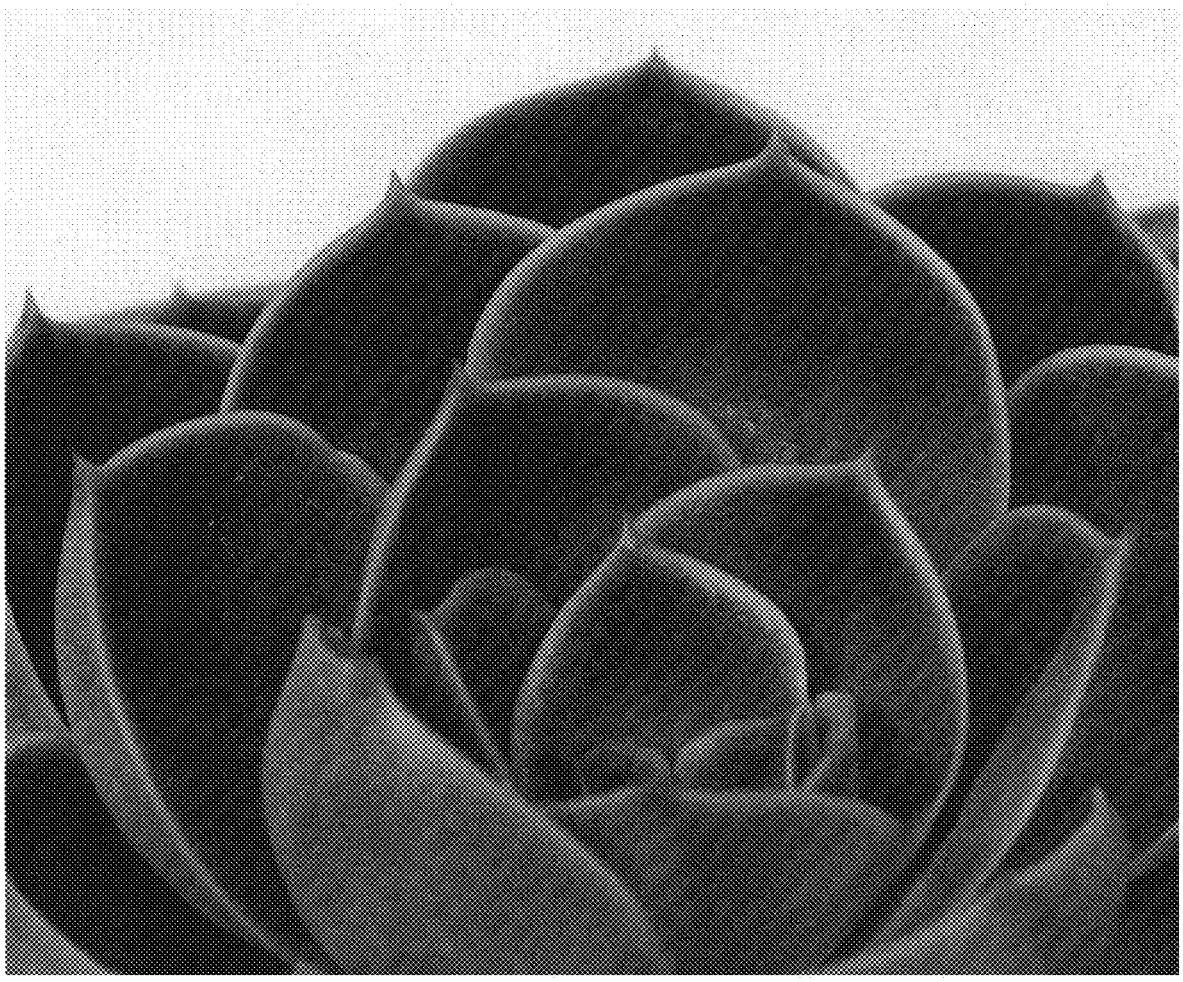
FIG. 3 illustrates, as nearly true as it is reasonably possible to make the same in color photographs of this type, the adaxial surface of the mature foliage 'AMIECH1913'.
Figure 4:
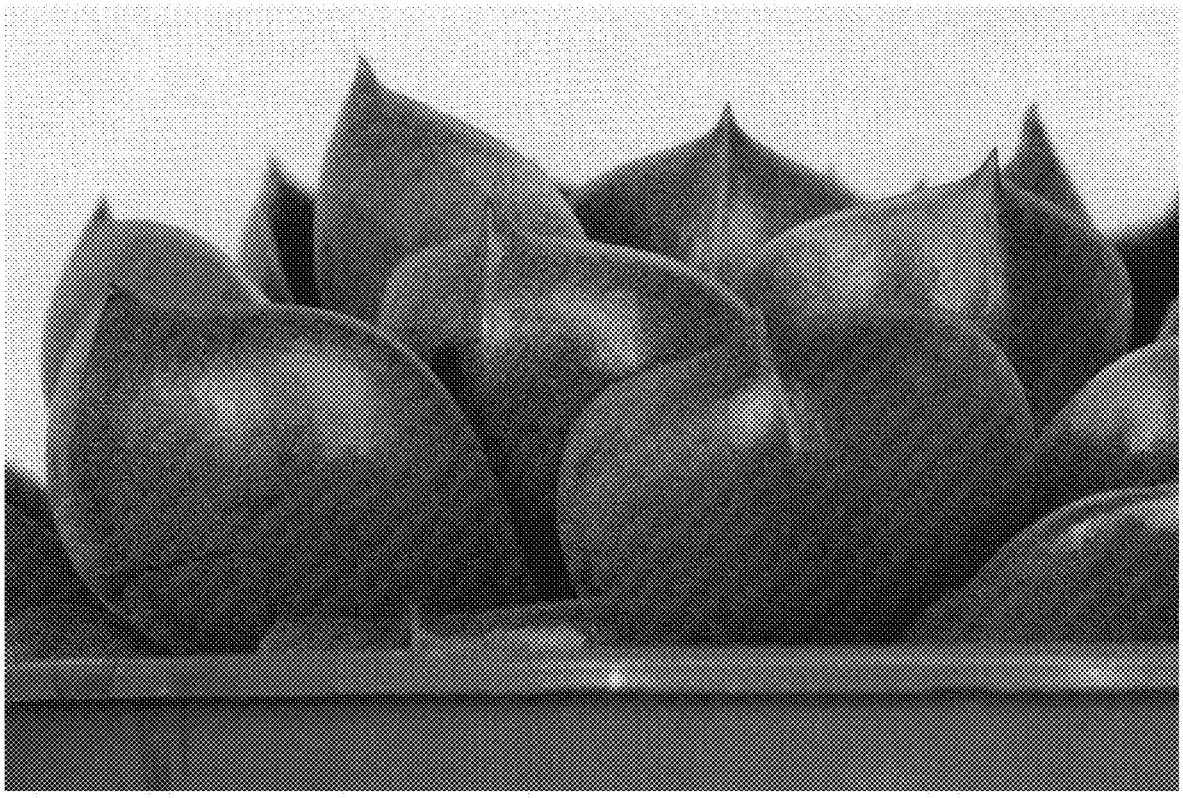
FIG. 4 illustrates, as nearly true as it is reasonably possible to make the same in color photographs of this type, the abaxial surface of the mature foliage 'AMIECH1913'.

The following observations and measurements made in January of 2020 describe averages from a sample set of six specimens of 8 months old 'AMIECH1913' plants grown in 11 cm nursery containers at commercial greenhouse in Heerhugowaard, the Netherlands. Plants were produced using conventional greenhouse production protocols for *Echeveria* plants which consisted of minimal irrigation and fertilizer applications, and chemical pest and disease control measures against mealy bug and *Botrytis* as required. Plants were grown under approximately 50 percent shade after propagation and later exposed to full sun once they began to mature. No photoperiodic treatments or artificial light was given to the plants.

Those skilled in the art will appreciate that certain characteristics will vary with older or, conversely, with younger plants. 'AMIECH1913' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart,* The Royal Horticultural Society, London, 2015 (sixth edition).

A botanical description of 'AMIECH1913' and comparisons with the parent plants and closest known comparator are provided below.

Plant description:

*Growth habit*.—Succulent perennial with foliage growing in a non-branched basal rosette.

*Plant shape*.—Flattened.

*Height from soil level to top of foliar plane*.—5.6 cm.

*Plant spread*.—Average of 10.2 cm.

*Growth rate*.—Moderately fast growing.

*Plant vigor*.—Moderately vigorous.

*Propagation*.—Type — Leaf cuttings. Time to initiate rooting — Approximately 21 days at 18 degrees Celsius. Crop time — Approximately 35 weeks to produce a marketable plant in a 7 cm container.

*Disease and pest resistance or susceptibility*.—Neither resistance nor susceptibility to typical *Echeveria* pests and diseases has been observed.

*Environmental tolerances*.—Adapt to, at least, USDA Zones 10 to 12 and temperatures as high as 40 degrees Celsius; moderate tolerance to rain yet drought tolerant once established; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 90 leaves per rosette.

*Shape*.—Obovate to short spatulate.

*Dimensions*.—4.8 cm long, 2.7 cm wide, and 0.5 cm thick, on average.

*Aspect*.—Strongly concave with an upward curled apex.

*Attitude*.—Juvenile foliage at the center of the rosette is held upward; foliage becomes progressively more relaxed towards the outer whorls of mature foliage.

*Apex*.—Apiculate.

*Base*.—Cuneate.

*Margin*.—Entire; not undulate.

*Pubescence, texture and luster of the adaxial surface*.—Glabrous, smooth, and matte; moderately glaucous.

*Pubescence, texture and luster of the abaxial surface*.—Glabrous, smooth, and matte; moderately glaucous.

*Color*.—Juvenile foliage, adaxial surface — Green, nearest to RHS NN137A; margined yellow-green, nearest to RHS 145A; the epicuticular glaucous wax covering the leaf surface is greyed-green, nearest to a mixture of RHS 191C and 191D. Juvenile foliage, abaxial surface — Yellow-green, nearest to RHS 147B; margined yellow-green, RHS 145A; the epicuticular glaucous wax covering the leaf surface is greyed-green, nearest to RHS 191C. Mature foliage, adaxial surface — Nearest to in between green and yellow-green, RHS NN137A and 147A, and fading to yellow-green towards the base, nearest to RHS 145B; margined yellow-green, nearest to a mixture of RHS 145A and 145B, and becoming darker towards the apex, nearest to RHS 152D; the epicuticular glaucous wax covering the leaf surface is greyed-green, nearest to a mixture of RHS 191C and 191D. Mature foliage, abaxial surface — Yellow-green, nearest to a mixture of RHS 147A and 147B; fading lighter towards the base, nearest to RHS 146D; margined yellow-green, nearest to a mixture of RHS 145A and 145B, and becoming darker towards the apex, nearest to RHS 152D; the epicuticular glaucous wax covering the leaf surface is nearest to greyed-green, nearest to RHS 191C. Venation — No venation is visible.

*Petiole*.—No petiole; leaves are sessile.

Inflorescence: No flowering has been observed to date.

Comparisons with the Parent Plant and Closest Known Comparator

Plants of the new cultivar 'AMIECH1913' differ from the seed parent, *Echeveria gilva* 'Green Gilva' (not patented), in the following characteristics described in Table 1 below.

TABLE 1

| Characteristic | 'AMIECH1913' | 'Green Gilva' |
|---|---|---|
| Plant size. | Larger than the parent. | Smaller than 'AMIECH1913'. |
| Foliage size. | Larger than the parent. | Smaller than 'AMIECH1913'. |
| Foliage aspect. | Strongly concave. | Flat; not concave. |
| General coloration of the foliage | Green and lightly suffused with greyed-green. | Green. |

Plants of the new cultivar 'AMIECH1913' differ from the pollen parent, an unnamed *Echeveria desmetiana* plant (not patented), in the following characteristics described in Table 2 below.

TABLE 2

| Characteristic | 'AMIECH1913' | The pollen parent. |
|---|---|---|
| Foliage aspect. | Strongly concave. | Flat; not concave. |
| General coloration of the foliage. | Green and lightly suffused with greyed-green. | Greyed-white. |
| Foliage durability. | More durable than the parent. | Less durable than 'AMIECH1913'. |

Comparisons with the Closest Known Comparator

Plants of the new cultivar 'AMIECH1913' differ from the closest known commercial comparator, *Echeveria* hybrid 'Imbricata' (not patented), in the following characteristics described in Table 3 below.

TABLE 3

| Characteristic | 'AMIECH1913' | 'Imbricata' |
|---|---|---|
| Foliage aspect. | Strongly concave. | Flat; not concave. |
| General coloration of the foliage. | Green and lightly suffused with greyed-green. | Blue-green. |

TABLE 3-continued

| Characteristic | 'AMIECH1913' | 'Imbricata' |
|---|---|---|
| Foliage durability. | More durable than the parent. | Less durable than 'AMIECH1913'. |

That which is claimed is:

1. A new and distinct variety of *Echeveria* hybrid plant named 'AMIECH1913', substantially as described and illustrated herein.

* * * * *